United States Patent [19]

Saltman et al.

[11] 3,985,709
[45] Oct. 12, 1976

[54] POLYMERIC COMPOSITIONS

[75] Inventors: William M. Saltman; Melvin Auerbach, both of Akron, Ohio

[73] Assignee: The Goodyear Tire & Rubber Company, Akron, Ohio

[22] Filed: May 12, 1975

[21] Appl. No.: 576,814

Related U.S. Application Data

[62] Division of Ser. No. 438,117, Jan. 30, 1974, Pat. No. 3,903,049.

[52] U.S. Cl. .................... 260/47 UA; 260/45.9 E; 260/814
[51] Int. Cl.² ........................................ C08L 7/00
[58] Field of Search .......... 260/47 UA, 45.9 E, 814

[56] References Cited
UNITED STATES PATENTS

| | | | |
|---|---|---|---|
| 3,629,197 | 12/1971 | Stiehl, Jr. | 260/47 |
| 3,767,628 | 10/1973 | Kline | 260/78 |
| 3,917,700 | 11/1975 | Auerbach | 260/45.9 E |

Primary Examiner—V.P. Hoke
Attorney, Agent, or Firm—F. W. Brunner; H. C. Young, Jr.

[57] ABSTRACT

An oxidation resistant polymeric composition comprising the reaction product of some carbon-to-carbon double bond unsaturated polymers and a 1,3-dipolar compound corresponding to the general formula

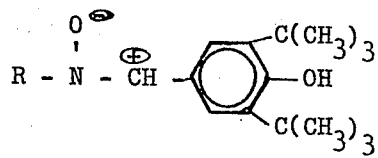

wherein R is selected from various alkyl radicals, aromatic radicals, cycloalkyl radicals, phenyl radicals and substituted phenyl radicals.

2 Claims, No Drawings

POLYMERIC COMPOSITIONS

This is a Division of application Ser. No. 438,117 filed Jan. 30, 1974 now U.S. Pat. No. 3,903,049.

This invention relates to age resistant polymeric compositions. More particularly, the invention relates to polymeric compositions that possess a high degree of resistance to the deleterious effects of oxidative aging.

Essentially all types of rubbers, both natural and synthetic, and particularly rubbers formed from dienes are known to be susceptible to deterioration resulting from prolonged exposure to oxidative aging. A great deal of effort has been expended by those engaged in the field of polymer technology to develop various stabilizers or antioxidants that will effectively inhibit the adverse effects of aging of these types of polymeric compositions. Many effective stabilizing materials, such as various aromatic amines and phenolic compounds have been developed to combat oxidative aging.

However, the prior art types of antioxidants, which are mixed into rubbers using conventional rubber compounding techniques, are subject to volatilization when the rubbers are exposed to elevated temperatures for prolonged periods of time. Also, many of the prior art antioxidants may be extracted from the rubbers if exposed to repeated contact with water or aqueous detergent solutions, for instance, when the rubber is exposed to weathering or is employed in wearing apparel. If the rubber containing the prior art antioxidant is subjected to organic solvents, the antioxidant may also be extracted.

It is therefore an object of this invention to provide polymeric materials, particularly rubbers, that are highly resistant to oxidative attack. It is an object to provide compositions in which the antioxidants are not subject to loss either by volatilization or extraction. Another object is to provide rubber compositions containing antioxidants which are chemically bound to the rubber. Further objects will become apparent as the description of the invention proceeds.

In accordance with the present invention there is provided an oxidation resistant polymer composition comprising the reaction product of (A) a rubbery polymer, having carbon-to-carbon double bond unsaturation in or pendant from the polymer chain, selected from the group consisting of (1) natural rubber, (2) homopolymers and copolymers of conjugated diolefins, (3) copolymers of conjugated diolefins and monovinyl-substituted aromatic hydrocarbons, (4) copolymers of conjugated diolefins and acrylonitrile, (5) copolymers of conjugated diolefins and alpha olefins, and (6) interpolymers of one or more lower alkyl α-olefins and a diene monomer, and (B) a 1,3-dipolar compound corresponding to the general formula

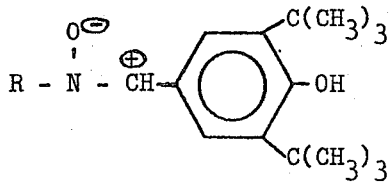

wherein R is selected from a group consisting of (1) alkyl radical containing from 1 to 12 carbon atoms, (2) condensed ring aromatic radicals, (3) cycloalkyl radicals, (4) a phenyl radical and (5) substituted phenyl radical containing at least one substituent from the group consisting of chlorine, bromine, iodine and fluorine atoms and alkyl, alkoxy, nitro, tertiary amino, cyano, carboxyl and carboalkoxy radicals.

The oxidation resistant polymeric compositions of the present invention are prepared by contacting a sulfur-curable rubbery polymer having carbon-to-carbon double bond unsaturation in the polymer chain with a 1,3-dipolar compound corresponding to the general formula above. The 1,3-dipolar compound adds to the polymeric material by means of a 1,3-dipolar cycloaddition reaction. This addition takes place across the carbon-to-carbon double bond of the polymeric material employed. The result of this addition is a polymeric composition containing five-membered heterocyclic rings in the polymer chain and having chemically bound thereto antioxidant functional groups. In other words, a polymeric composition possessing built-in antioxidant characteristics.

The 1,3-dipolar cycloaddition reaction is generally and conveniently carried out by mixing the polymeric material and the 1,3-dipolar compound together in an inert solvent, heating this reaction mixture to the reflux temperature and maintaining the reaction mixture at said temperature, with continuous agitation, until the addition reaction is complete. Solvents suitable for preparing the oxidation resistant polymeric compositions of the present invention are those inert hydrocarbon solvents selected from a group consisting of aliphatic, cycloaliphatic and aromatic hydrocarbons. By the term "inert" is meant that the solvent employed neither interferes with the cycloaddition reaction nor enters into the structure of the resultant product of the cycloaddition reaction. Representative examples of suitable inert hydrocarbon solvents include hexane, heptane, cyclohexane, benzene, toluene and the like.

As noted previously, the temperatures at which the 1,3-dipolar cycloaddition reactions are usually carried out are the reflux temperatures or more specifically the boiling point temperatures of the various solutions employed. It can be seen that the reaction temperatures may vary over a wide range. Therefore, the reaction temperature is not a critical parameter in preparing the polymeric compositions of this invention. However, it is generally preferred to employ solvents having high boiling points since higher temperatures generally give faster reaction rates. By the term "high" is meant temperatures of 67° C. or higher.

The reaction time required to obtain the polymeric compositions of this invention are of course dependent upon the temperatures at which the reactions are carried out and also upon the relative reactivity of the particular 1,3-dipolar compound employed toward the particular polymeric material employed. Generally it has been found that good results are obtained over a period of time ranging from a few hours to several days.

The amount of the 1,3-dipolar compounds, corresponding to the general formula above, employed to form the oxidative resistant polymeric compositions of this invention can also vary over a wide range, but must be at least a stabilizing amount. Satisfactory results may be obtained with weight ratios ranging from about 0.01 part per hundred parts of rubber (phr) to about 5 phr. A more preferred range is one from about 0.1 phr to about 2.0 phr.

The 1,3-dipolar compounds useful in preparing the oxidation resistant polymeric compositions of the present invention are those 1,3-dipolar compounds corresponding to the general formula above and which may be prepared by the reaction of a nitroso compound corresponding to the formula R–N=O where R is selected from the group consisting of (1) alkyl radical containing from 1 to 12 carbon atoms, (2) condensed ring aromatic hydrocarbon radicals, (3) cycloalkyl radicals, (4) phenyl radical and (5) substituted phenyl radical containing at least one substituent selected from the group consisting of chlorine, bromine, iodine and fluorine atoms and alkyl, alkoxy, nitro, tertiary amine, cyano, carboxy and carboalkoxy radicals, with 3,5-di-t-butyl-4-hydroxybenzyl pyridinium chloride. In general, these reactions may be carried out in any suitable inert organic solvent. By the term "inert" is meant that the solvent neither enters into the structure nor interferes with the preparation of the desired antioxidant. Suitable inert solvents include alcohols such as methanol, ethanol, isopropanol and the like, ethers such as dioxane, tetrahydrofuran and the like, and ketones and nitriles such as acetone, acetonitrile and the like. Mixtures of the above solvents may also be employed with satisfactory results. The amount of solvent employed may range from about 2 to about 20 times the weight of the reactants present. Representative examples of the 1,3-dipolar compounds which can be prepared by the above described reaction include:

1-(3,5-di-t-butyl-4-hydroxyphenyl)-N-naphthyl nitrone;
1-(3,5-di-t-butyl-4-hydroxyphenyl)-N-phenyl nitrone;
1-(3,5-di-t-butyl-4-hydroxyphenyl)-N-butyl nitrone;
1-(3,5-di-t-butyl-4-hydroxyphenyl)-N-(2-bromobutyl)-nitrone;
1-(3,5-di-t-butyl-4-hydroxyphenyl)-N-cyclohexyl nitrone;
1-(3,5-di-t-butyl-4-hydroxyphenyl)-N-(4-nitrophenyl)-nitrone;
1-(3,5-di-t-butyl-4-hydroxyphenyl)-N-(3-ethylphenyl)-nitrone;
1-(3,5-di-t-butyl-4-hydroxyphenyl)-N-tolyl nitrone; and
1-(3,5-di-t-butyl-4-hydroxyphenyl)-N-(2-ethoxyphenyl)nitrone.

The sulfur-curable rubbery polymers useful in preparing the oxidation resistant polymeric compositions of this invention are those rubbery polymers having carbon-to-carbon double bond unsaturation in or pendant from the polymer chain. Said polymers include natural rubber, homo- and co-polymers of conjugated diolefins, copolymers of conjugated diolefins and monovinyl-substituted aromatic hydrocarbons, copolymers of conjugated diolefins and acrylonitrile, copolymers of conjugated diolefins and alpha olefins and polymers of lower alkyl alpha olefins and diene monomers. They also include polymers or copolymers prepared by ring opening of one or more cyclic monomers such as polypentenamer, polyoctenamer, etc.

Representative examples of the above rubbery polymers include natural rubber, polybutadiene, polyisoprene, butadiene/isoprene copolymers, butadiene/styrene and isoprene/styrene copolymers, butyl rubber which is prepared from a mixture of a major proportion of isobutylene and a minor proportion of a conjugated diolefin, butadiene/acrylonitrile copolymer, butadiene/ethylene copolymer, ethylene/propylene/1,4-hexadiene terpolymer and the like.

The following examples are representative of the invention and are not intended to be restrictive in their nature as to the scope.

EXAMPLE I

To a clean dry 250 ml. round bottom 3-neck flask equipped with a magnetic stirrer, thermometer and addition funnel was added 6.69 g. (0.02 mole) of 3,5-di-t-butyl-4-hydroxy-benzylpyridinium chloride in 100 ml. of ethanol and 2.36 g. (0.022 mole) of nitrosobenzene. The clear solution was cooled to 0° to 5° C. and sodium hydroxide (2.45 g.; 0.06 mole) in 60 ml. of water was added dropwise in 40 minutes. The reaction mixture was stirred an additional 3 hours at ambient temperature and then diluted with 50 ml. water, filtered, and the collected product dried to yield 5.07 g. (79.2% yield) of 1-(3,5-di-t-butyl-4-hydroxyphenyl)-N-phenyl-nitrone, MP-137°–140° C.

The theoretical amount of carbon, hydrogen and nitrogen in the nitrone compound was calculated to be 77.49%, 8.37% and 4.30% respectively. An analysis of the compound for carbon, hydrogen and nitrogen found it to actually be 77.54%, 8.46% and 4.22% respectively.

EXAMPLE II

This example shows how various antioxidant compounds, including the compound of this invention, were added to polybutadiene rubber and the resulting antioxidant effect.

The polybutadiene rubber was dissolved in benzene and mixed at room temperature with the various antioxidants enumerated in Table 1. The resulting polymer cements were evaporated to dryness and the polymers were submitted for oxygen absorption at 100° C.

The higher the number of hours required to reach one percent oxygen absorption, the more effective the compound is against oxidative attack.

Table 1

Evaluation of Various Nitrogen-Oxygen Compounds as Antioxidants[1]

| | Hours to 1% Oxygen Absorption | |
|---|---|---|
| | 0.5 phr | 1.0 phr |
| | 1.4 | 1.4 |

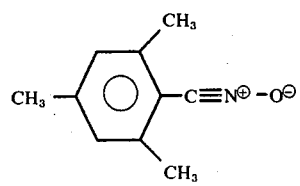

2,4,6-trimethylbenzonitrile-N-oxide

Table 1-continued
Evaluation of Various Nitrogen-Oxygen Compounds as Antioxidants[1]

| | Hours to 1% Oxygen Absorption | |
| --- | --- | --- |
| | 0.5 phr | 1.0 phr |
| 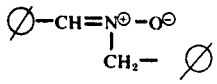<br>α-phenyl-N-benzyl nitrone | 5.3 | 8.0 |
| 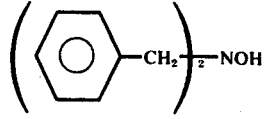<br>N,N-dibenzyl hydroxylamine | 22.0 | 25.0 |
| 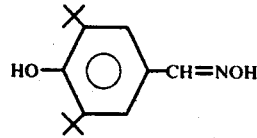<br>3,5-di-t-butyl-4-hydroxy benzaldehyde oxime | 60.0 | 198.0 |
| 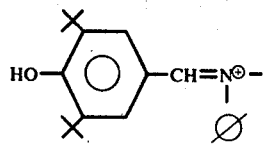<br>1-(3,5-di-t-butyl-4-hydroxyphenyl)-N-phenyl nitrone | 99.0 | 217.0 |
| 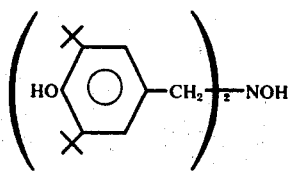<br>N,N-bis(3,5-di-t-butyl-4-hydroxybenzyl) hydroxylamine | 118.0 | 268.0 |
| 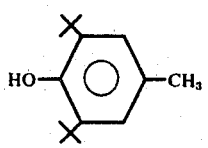<br>2,6-di-t-butyl-4-methyl phenol | 392.0 | 471.0 |

[1]All compounds were added to the polymer cement.

EXAMPLE III

The inventive compound was added to polybutadiene in benzene at various concentrations and reacted for varying times at 80° C. as illustrated in Table 2. The inventive compound can undergo a chemical reaction to build itself into the rubber compound.

This example illustrates the built-in antioxidant effect of the claimed compounds as compared to other antioxidant compounds that are not of the built-in type and how the nonbuilt-in compounds may be extracted and lose their effectiveness as compared to the inventive compounds.

The compound 3,5-di-t-butyl-p-cresol is considered to be a good antioxidant but like many others, has the disadvantage of being volatile. Table 2 illustrates how the antioxidant qualities of the 3,5-di-t-butyl-p-cresol is lost when compared with the claimed built-in antioxidant. The time to 1% oxygen absorption is an illustration of the antioxidant effectiveness of a compound, as can be seen in Table 2. When rubber containing 3,5-di-t-butyl-p-cresol is extracted with acetone the antioxidant's effectiveness is greatly reduced, whereas the inventive compounds are still very effective.

Table 2

| | Antioxidant | phm Added* | Moles per 100g Rubber* | Reaction Time, Days | Time to 1% $O_2$ Absorption, hrs* |
|---|---|---|---|---|---|
| 1 | HO–⌬(X,X)–CH=N⁺(O⁻)–Ph | 0.96 | $1.82 \times 10^{-4}$ | 7 | 54.3 |
| 2 | " | 1.25 | $2.34 \times 10^{-4}$ | 15 | 134.9 |
| 3 | " | 1.80 | $3.47 \times 10^{-4}$ | 7 | 136.1 |
| 4 | " | 1.91 | $3.66 \times 10^{-4}$ | 15 | 216.3 |
| 5 | HO–⌬(X,X)–CH₃ | 1.58 | $4.54 \times 10^{-4}$ | — | 28.5 |
| 6 | " | 1.73 | $4.54 \times 10^{-4}$ | — | 170.2 |

*Samples 1–5 were extracted with acetone for 48 hrs. Sample 6 was not extracted. Antioxidant content calculated from nitrogen analysis.

While certain representative embodiments and details have been shown for the purpose of illustrating the invention, it will be apparent to those skilled in this art that various changes and modifications may be made therein without departing from the spirit or scope of the invention.

What is claimed is:

1. An oxidation resistant polymeric composition comprising the reaction product of (A) a sulfur-curable rubbery polymer having carbon-to-carbon double bond unsaturation in the polymer chain selected from the group consisting of (1) natural rubber, (2) copolymers of conjugated diolefins and monovinyl-substituted aromatic hydrocarbons, (3) copolymers of conjugated diolefins and acrylonitrile, (4) copolymers of α-olefins and conjugated diolefins, (5) interpolymers of one or more lower alkyl α-olefins and a diene monomer, and (6) polymers or copolymers prepared by ring opening of one or more acyclic monomers, and (B) a 1,3-dipolar compound corresponding to the general formula

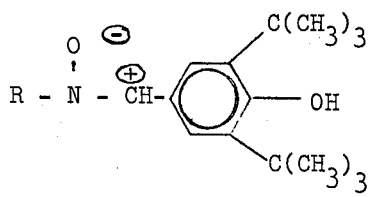

wherein R is selected from a group consisting of (1) alkyl radicals containing from 1 to 12 carbon atoms, (2) naphthyl radicals, (3) cycloalkyl radicals, (4) phenyl radicals, and (5) substituted phenyl radicals containing at least one substituent selected from the group consisting of chlorine, bromine, iodine and fluorine atoms and alkyl, alkoxy, nitro, tertiary amino, cyano, carboxy and carboalkoxy radicals.

2. An oxidation resistant polymeric composition comprising the reaction product of (A) a sulfur-curable rubbery polymer having carbon-to-carbon double bond unsaturation in or pendant from the polymer chain selected from the group consisting of (1) natural rubber, (2) copolymers of conjugated diolefins and monovinyl substituted aromatic hydrocarbons, (3) copolymers of conjugated diolefins and acrylonitrile, (4) copolymers of α-olefins and conjugated diolefins, (5) interpolymers of one or more lower alkyl α-olefins and a diene monomer, (6) polymers or copolymers prepared by ring opening of one or more acyclic monomers, and (B) a 1,3-di-polar compound selected from the group consisting of 1-(3,5-di-t-butyl-4-hydroxyphenyl)-N-naphthyl nitrone, 1-(3,5-di-t-butyl-4-hydroxyphenyl)-N-phenyl nitrone, 1-(3,5-di-t-butyl-4-hydroxyphenyl)-N-butyl nitrone, 1-(3,5-di-t-butyl-4-hydroxyphenyl)-N-(2-bromohexyl) nitrone, 1-(3,5-di-t-butyl-4-hydroxyphenyl)-N-cyclohexyl nitrone, 1-(3,5-di-t-butyl-4-hydroxyphenyl)-N-(4-nitrophenyl) nitrone, 1-(3,5-di-t-butyl-4-hydroxyphenyl)-N-(3-ethyl phenyl) nitrone, 1-(3,5-di-t-butyl-4-hydroxyphenyl)-N-tolyl nitrone, and 1-(3,5-di-t-butyl-4-hydroxyphenyl)-N-(2-ethoxy phenyl) nitrone.

* * * * *